United States Patent
Loreth

(10) Patent No.: US 8,834,799 B2
(45) Date of Patent: Sep. 16, 2014

(54) AIR CLEANING APPARATUS

(75) Inventor: Andrzej Loreth, Akersberga (SE)

(73) Assignee: Cair AB, Akersberga (SE)

( * ) Notice: Subject to any disclaimer, the term of this patent is extended or adjusted under 35 U.S.C. 154(b) by 314 days.

(21) Appl. No.: 13/119,284

(22) PCT Filed: Sep. 24, 2009

(86) PCT No.: PCT/SE2009/000421
§ 371 (c)(1),
(2), (4) Date: Mar. 16, 2011

(87) PCT Pub. No.: WO2010/036176
PCT Pub. Date: Apr. 1, 2010

(65) Prior Publication Data
US 2011/0171075 A1 Jul. 14, 2011

(30) Foreign Application Priority Data
Sep. 24, 2008 (SE) .................................. 0802026

(51) Int. Cl.
*A61L 9/22* (2006.01)
*B03C 3/12* (2006.01)
*B03C 3/41* (2006.01)

(52) U.S. Cl.
CPC ... *B03C 3/12* (2013.01); *A61L 9/22* (2013.01); *B03C 3/41* (2013.01)
USPC .................. 422/121; 96/63; 96/68; 96/81

(58) Field of Classification Search
CPC ............. A61L 9/16; A61L 9/18; A61L 9/22
USPC .......... 422/121; 96/62, 63, 68, 81, 60, 69, 78, 96/95–98
See application file for complete search history.

(56) References Cited

U.S. PATENT DOCUMENTS

| 4,313,741 | A | 2/1982 | Masuda et al. |
| 5,330,559 | A * | 7/1994 | Cheney et al. ................ 96/68 |
| 5,980,614 | A | 11/1999 | Loreth et al. |
| 5,993,521 | A | 11/1999 | Loreth et al. |
| 6,203,600 | B1 | 3/2001 | Loreth |
| 6,398,852 | B1 | 6/2002 | Loreth |
| 2007/0041882 | A1 * | 2/2007 | Roseberry et al. ......... 422/186.3 |

FOREIGN PATENT DOCUMENTS

| DE | 202004012352 U1 | 11/2004 |
| JP | 2008295937 A | 12/2008 |

OTHER PUBLICATIONS

International Search Report, dated Dec. 2, 2009, from corresponding PCT application.

* cited by examiner

*Primary Examiner* — Timothy Cleveland
(74) *Attorney, Agent, or Firm* — Young & Thompson

(57) ABSTRACT

An air cleaning apparatus includes an air flow duct, with an extent in an axial direction, to accommodate air flow entering the apparatus, an air-conveying fan unit disposed in the air flow duct, a precipitator connected to a high-voltage source and with a throughflow passage for air to be cleaned. The precipitator includes two electrode elements or two groups of electrode elements, each of the respective two being connected to a respective pole of the high-voltage source, and a unipolar corona electrode disposed close to one end of the air flow duct. A target electrode is disposed at radial spacing from the corona electrode, the corona electrode being so disposed that the ions generated at it can freely spread away from the corona electrode towards the target electrode, and that the target electrode surrounds the air flow entering the apparatus.

20 Claims, 2 Drawing Sheets

AIR CLEANING APPARATUS

TECHNICAL FIELD OF THE INVENTION

The present invention relates to an air cleaning apparatus, in particular an apparatus for cleaning of room air, here meaning air in residential spaces, offices or industrial premises, but also for cleaning of outside air. More specifically, the invention relates to an air cleaning apparatus for cleaning of indoor air and/or outdoor air, which apparatus comprises an air flow duct, with an extent in an axial direction, to accommodate the air flow entering the apparatus, an air-conveying fan unit disposed in the air flow duct, a precipitator connected to a high-voltage source and with a throughflow passage for air which is to be cleaned, which precipitator comprises two electrode elements or two groups of electrode elements, each of the respective two being connected to a respective pole of the high-voltage source, and a unipolar corona electrode disposed close to one end of the air flow duct.

STATE OF THE ART

There are known apparatuses in the form of two-stage electric filters in which an ionisation device takes the form of a corona electrode and a target electrode/counter electrode which together constitute an ionisation chamber. The ionisation chamber, which is often constituted by the walls of the target electrode, delineates a well-defined space within which the charging of the dust particles in the air takes place in the more or less immediate vicinity of a separator which forms part of the two-stage electric filter and which is often referred to as a precipitator. The effectiveness of such air cleaning devices, so-called two-stage filters, depends to a very great extent on the effectiveness of the ionisation chamber. One way of achieving effective charging of the airborne dust is to drive the corona electrode with powerful corona current, but this results also in an undesirable powerful ozone emission. Certain manufacturers of two-stage electric filters, e.g. Oreck in the U.S.A., use a special ozone filter to deal with this problem.

Another way of achieving effective charging but low ozone emission, i.e. with low corona current, is to configure the ionisation chamber in such a way that the charging space delineated by the target electrode of the ionisation chamber, through which space the airborne particles pass on their way to the precipitator, is of great extent in the air flow direction. The dwell time of the particles in this region thus becomes relatively long, with the consequence that the time available for the charging is also relatively long. U.S. Pat. No. 5,993,521 indicates a two-stage electric filter in which this way of achieving effective charging is implemented.

However, there are disadvantages of the ionisation chamber configuration according to that patent, viz. the physical volume of the ionisation chamber, which results in relatively voluminous apparatuses. This is particularly sensitive in the case of using high-resistance precipitators as described for example in U.S. Pat. No. 6,203,600, which afford the possibility of configuring relatively large circular precipitators with a diameter of up to 100 cm or more. A matching ionisation chamber for such a circular precipitator is with advantage tubular, with diameter and length, measured in the air flow direction, corresponding to the diameter of the precipitator.

Over recent years the debate about indoor environments and their impact on human health has increasingly focused on the presence of particles in air inhaled. In this context there has been a great increase in interest in so-called freestanding air cleaners to complement traditional ventilation systems. This entails exacting requirements for the ability of the apparatuses to significantly reduce airborne pollution without harmful generation of ozone and with low noise levels and low energy consumption. There are also requirements with regard to adapting the apparatuses to indoor environments, including their size, suitable siting potential and, not least, easy servicing.

U.S. Pat. No. 6,398,852 presents a device of the kind indicated in the introduction with the object, on the basis of preferred embodiments, of reducing the dimensions of the air cleaning apparatus in the air flow direction through the apparatus in cases where circularly symmetrical precipitators configured in accordance with U.S. Pat. No. 6,203,600 which maintain low ozone generation are used. The effectiveness of the device does of course depend on the air flow dwell time in the ionisation chamber and on the corona current.

Another way of achieving effective charging of airborne dust by means of a very low corona current is described in U.S. Pat. No. 5,980,614. According to that invention, a corona electrode in the form of a unipolar ion source (brush/point) is disposed close to a device which comprises a precipitator, a fan and a high-voltage source, which corona electrode is so disposed that the ions generated at it are substantially able to spread freely from the corona electrode into the space which contains the air mass which is to be cleaned. Thus the space in which the device is situated constitutes a large ionisation chamber. In relative terms, the dwell time for the particles is therefore very long, which makes it possible to use an extremely low corona current. The latter may be less than 1 microampere, which in comparative terms is a very low current. That way of causing effective charging of aerosol particles by extremely low corona discharge certainly works, but there are disadvantages with such a solution. Not only may dirt particles deposit themselves upon the walls of the room, but persons who are in the vicinity of the device may also become electrically charged, which is not inherently dangerous but may be felt to be unpleasant.

In this context it is important to note that the requirements for effective charging of particles for cleaning by so-called two-stage electric filters are quite distinct from the requirements for cleaning of particles in a room with so-called ionisers. The effectiveness of particle charging for a device with a fan and for a precipitator, i.e. the effectiveness of a two-stage electric filter, needs to match the velocity of the air flow through such a device, since otherwise the air cleaning capacity will be low, as only electrically charged particles (aerosols) can be separated in a precipitator. Charging and cleaning of particles by means of an ioniser, with or without a particle-attracting electrode disposed at the ioniser casing, involve no such requirements. Such devices are dimensioned so that the ion cloud from the corona electrode may spread freely in the space in which the device is situated.

OBJECTS AND FEATURES OF THE INVENTION

A primary object of the present invention is to propose a two-stage electric filter of the kind defined in the introduction which achieves effective separation of airborne dust (aerosols) by using extremely low corona current, more specifically corresponding to the levels of corona current which are applicable in devices with unipolar corona electrodes (brush/point) and free ion migration in the room, see for example U.S. Pat. No. 5,980,614.

A further object of the present invention is to minimise the extent of the electric filter in the air flow direction.

At least the primary object of the present invention is achieved by a device provided with the features indicated in the independent claim 1 set out below. Preferred embodiments of the invention are defined in the dependent claims.

BRIEF DESCRIPTION OF THE DRAWINGS

Preferred embodiments of the invention are described below with reference to the attached drawings, in which.

DETAILED DESCRIPTION OF PREFERRED EMBODIMENTS OF THE INVENTION

Figure 1:
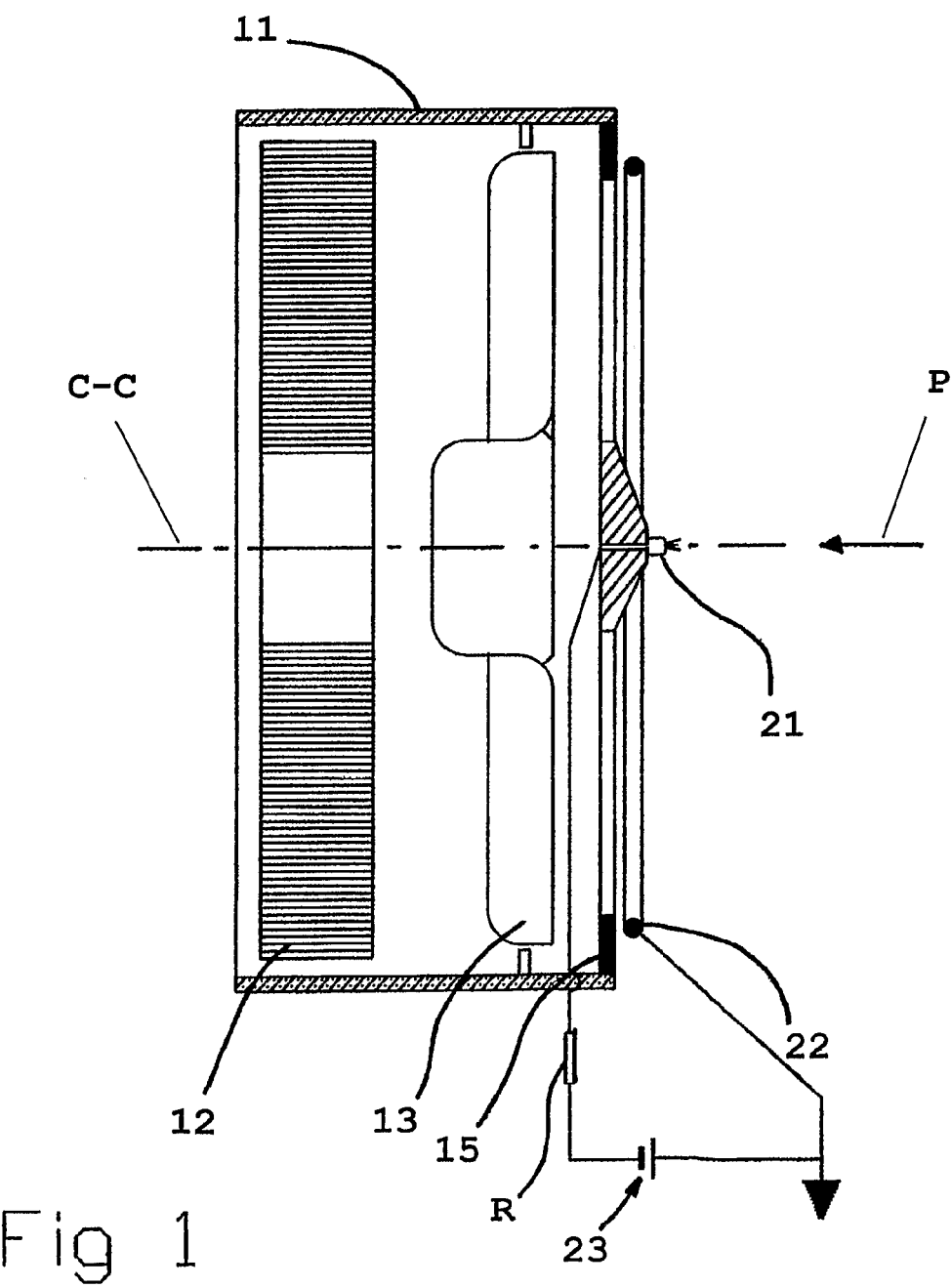
FIG. 1 depicts a schematic and partly sectional view of a first embodiment of the electric filter according to the present invention.

The air cleaning apparatus depicted in FIG. 1 takes the form of a two-stage electric filter which comprises a preferably circular cylindrical casing 11 which serves also as air flow duct. The axis C-C in FIG. 1 defines the axial direction of the electric filter and also constitutes a centreline. The electric filter comprises also a readily interchangeable and preferably circular cylindrical electrostatic precipitator 12 disposed in the casing 11, and an air-conveying device in the form of a fan/fan unit 13 which serves to convey air through the device. The precipitator 12 is configured in accordance with the description in U.S. Pat. No. 6,203,600 whereby the precipitator 12 is cylindrical and made of high-resistance material. U.S. Pat. No. 6,203,600 describes also how a precipitator of the relevant kind is connected to a high-voltage source, and that specification is therefore incorporated by reference. U.S. Pat. No. 6,203,600 should be referred to as regards the connection of the precipitator 12 to a high-voltage source 23 which is described below.

The electric filter comprises also an inlet grille 15 so configured that it acts like a coarse mechanical filter, i.e. large particles in the air will be caught in the inlet grille 15. The inlet grille 15 is made of insulating material, preferably plastic, and is pervious to air flow.

A unipolar corona electrode 21 with axial extent is disposed in the form of a carbon fibre brush in the centre of the portion of the inlet grille 15 which is pervious to air flow. A circular counter electrode/target electrode 22 which is symmetrical with respect to the corona electrode 21 is disposed in the form of a ring in the region of the periphery of the inlet grille 15 and at radial spacing from the corona electrode 21. FIG. 1 depicts schematically how the corona electrode 21 is connected to a negative first pole of a high-voltage source 23 and the target electrode 22 is connected to a second pole of the high-voltage source 23, which second pole is electrically earthed.

The air flow generated by the fan 13, represented by the arrow P in FIG. 1, thus passes through the inlet grille 15 of the electric filter, past the fan 13 and through the precipitator 12.

Laboratory tests have shown that even an extremely small corona current, less than 1 microampere, is sufficient to achieve effective charging of the particles (aerosols), i.e. for achieving high separation of them in the downstream precipitator 12. What is surprising with this arrangement is that a majority of the corona current (in the form of an ion cloud) generated at the corona electrode 21 reaches the target electrode 22 instead of, as in the case of the device according to U.S. Pat. No. 5,980,614, migrating into the room in which the device is situated. As the magnitude of the corona current (a fraction of a microampere) corresponds to the values in accordance with U.S. Pat. No. 5,980,614, this means that it is still perfectly sufficient to ensure that charging of particles takes place in the vicinity of the inlet area of the device and that free migration of ions into the space in accordance with U.S. Pat. No. 5,980,614 has substantially no appreciable effect on the charging of particles.

The very high separation effectiveness in combination with extremely low corona current indicates a certain expansion of the ion cloud from the corona electrode 21, away from the inlet area of the electric filter, i.e. in a direction opposite to the air flow, so that particles in the air flow which pass the inlet to the electric filter have sufficient dwell time to acquire an electrical charge. Laboratory tests have shown that a majority of the expansion of the ion cloud between the corona electrode 21 and the target electrode 22 takes place perpendicularly out from the plane which the target electrode 22 defines and in the opposite direction to the air flow direction P. The expansion of the ion cloud in the opposite direction to the air flow direction P reaches at most a distance corresponding to the radial spacing between the corona electrode 21 and the target electrode 22. The expansion of the ion cloud from the corona electrode 21 will also be easy to regulate by selecting the voltage of the target electrode 22.

If the target electrode 22 is connected to a pole of the high-voltage source whose polarity in relation to earth potential is opposite to the voltage of the corona electrode, the expansion of the ion cloud from the corona electrode 21 to the target electrode 22 is reduced. The reason is that upon such energisation of the electrodes 21 and 22 in combination with the extremely low corona current, the surfaces of the room will act as electrostatic shield electrodes or reflector electrodes, i.e. the ion cloud generated between the corona electrode 21 and the target electrode 22 will be prevented, by the room's electrical status relative to the target electrode 22, from migrating to the surfaces of the room. The expansion of the ion cloud from the corona electrode 21 can therefore be regulated, as also the dwell time for the passage of the air flow through the ion cloud.

The ever-increasing requirements for low or negligible ozone generation and hence exceptionally low levels of corona current have the effect that the electrostatic field between the corona electrode 21 and the target electrode 22 should not be disturbed by other conductive and energised parts of the device which might draw to themselves part of the corona current and hence increase ozone generation. Such parts may include the precipitator 12, particularly if it is situated upstream of the fan 13 and therefore nearest to the corona electrode 21. The blades of the fan 13, its motor and its frame are also such parts if they are made of conductive material. To prevent this phenomenon, the blades and any frame of the fan 13 depicted by way of example in FIG. 1 are made of plastic.

If the precipitator 12 is situated near to the inlet aperture of the electric filter, the precipitator 12 may be protected from receiving part of the corona current by, for example, a surface of electrically insulating material of foam plastic type or the like, which surface may have air flowing through it.

In the embodiment depicted in FIG. 1, the target electrode 22 takes the form of a wire ring disposed close to the inlet grille 15. Other embodiments of the target electrode may of course be used, e.g. they may have a certain extent in the air flow direction or in a radial direction. It is important, however, that the target electrode 22 should substantially enclose/surround the whole of the air flow which is intended to be cleaned and that the target electrode 22, given the location and energisation of the corona electrode 21, is in terms of field (electrostatic field) substantially circular and symmetrical relative to the corona electrode 21. This means that the ion cloud generated will be similar, as viewed radially from the location of the corona electrode 21.

As regards target electrodes 22 with a large diameter that are adapted to applying voltages distinct from nil, it may be practical to divide the target electrode 22 into a plurality of parts electrically insulated from one another and each connected to the high-voltage source via separate high-resistance resistors. This will reduce the capacitive energy stored in the target electrode 22 and hence also the discharge energy arising upon a possible short-circuit or touch. For these reasons, the target electrode 22 in accordance with the invention may with advantage be made of dissipative or semi-conductive material or be provided with a coating of dissipative or semi-conductive material.

The present invention is not limited to circular precipitators. Other shapes of precipitator may be used, but what is essential is that the electrostatic field round the corona electrode 21 is circularly symmetrical, which can most easily be achieved with a unipolar corona electrode 21 and a circularly symmetrical target electrode 22, and that the ion cloud generated round the corona electrode 21 can freely fill the space in the vicinity of the electric filter's inlet area. The two-stage electric filter according to the invention whose characteristics are indicated in the claims thus has both an ionisation electrode/corona electrode 21 and a target electrode 22, which components may together be regarded as constituting an ionisation chamber without any physical limitation in the counterflow direction. In other words, the physical dimensions of the electric filter's ionisation chamber are many times greater than the "disc-like" ionisation chamber defined by the circular target electrode 22 and the corona electrode 21.

It should be noted that the electric filter also works in cases where the expansion of the ion cloud to some extent fails to reach the target electrode 22 but instead reaches other conductive and energised parts of the electric filter. However, this will be at the cost of a higher corona current, i.e. greater ozone emission without improving the electric filter's efficiency, i.e. its particle separation effectiveness.

The inlet grille 15 depicted in FIG. 1 is not a necessary part of this invention. The unipolar corona electrode 21 may be situated substantially in the symmetry axis of the target electrode 22 at the inlet to the air flow duct and followed, as viewed in the air flow direction through the duct, of for example the precipitator 12. It is essential that the corona electrode 21 is axially directed and points in the opposite direction to air flow through the duct, i.e. towards the surroundings. If the inlet grille 15 is dispensed with, it is important that precipitator 12 is screened relative to the corona electrode 21, e.g. by an electrically insulated surface between the corona electrode 21 and the precipitator 12.

Laboratory tests have shown that it is the portion of the target electrode 22 situated nearest to the corona electrode 21 which receives the most corona current. The particular shape of the target electrode 22 is therefore of minor significance if it comprises not only the circularly symmetrical portion facing towards the corona electrode 21 but also other portions which extend further away from the corona electrode 21.

It is of course not necessary to use a carbon fibre brush 21 as corona electrode. A point or some other known form of unipolar short corona may also be used. Opposite polarity, i.e. positive corona and negative voltage on the target electrode 22, may also be applicable.

The open ionisation chamber and the expansion of the ion cloud towards the target electrode 22 create, as viewed from the corona electrode 21 towards the target electrode 22, a nearly hemispherical region (dwell space) in which there is risk of electrostatic charging. This is not dangerous but may be felt to be unpleasant. The present invention makes it possible to significantly minimise this risk. This possibility is surprisingly afforded by the extremely low corona current. This is achieved by extremely high resistances R situated between the poles of the high-voltage source and the connection to the corona electrode 21 and/or the target electrode 22. In FIG. 1, only one resistor R is placed between the high-voltage source H and the corona electrode 21.

Laboratory tests have shown that a significant effect can be achieved at even only about 1 Gohm resistance R, but the resistance value may preferably be greater than 2 Gohm. The greater the resistance value, the longer the time for which any part of the body, e.g. hands, may remain in the vicinity of the corona electrode 21 without risk of electrostatic charging. This is extremely important from a comfort point of view and only possible in practice at corona currents representing a fraction of a microampere. By way of example it may be mentioned that a corona current of 0.1 microampere×10 Gohm resistance results in a voltage drop of only 1 kV, as against an approximately 7-8 kV voltage drop between the corona electrode 21 and the target electrode 22 if they are situated at a mutual radial spacing of 15 cm. In other words, the voltage increase across the protective resistor (10 Gohm) which has to be taken into account in designing the high-voltage unit for the purpose is only about 10% of the respective voltage drop across the protective resistor. Should the corona current necessary for sufficient particle charging be of the order of 3 microamperes, which is also extremely small in the context, the voltage drop across the protective resistor R will represent 30 kV, which would be unreasonably large with respect to production cost and other electrical operating parameters.

Figure 2:
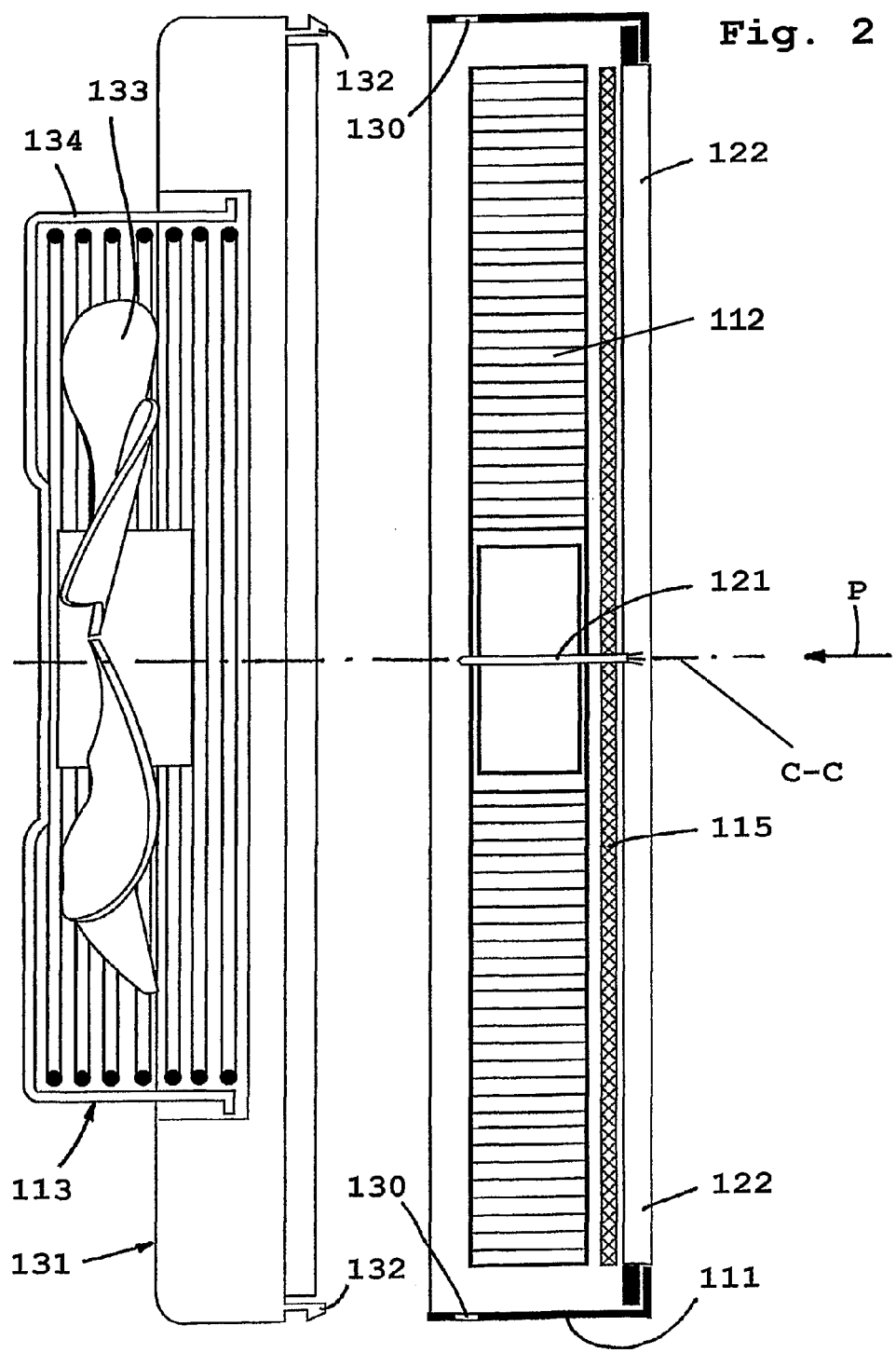
FIG. 2 depicts a schematic exploded view of the constituent parts of an alternative embodiment of the electric filter according to the present invention.

The alternative embodiment depicted in FIG. 2 of an air cleaning apparatus according to the present invention comprises a preferably circular cylindrical casing 111, the axial direction of which is denoted by the axis C-C, which axis constitutes also the centreline of the casing 111. The casing 111 serves as air flow duct. The casing 111 accommodates a precipitator 112 configured in accordance with the description in U.S. Pat. No. 6,203,600, whereby the precipitator 112 is cylindrical and made of high-resistance material. A unipolar corona electrode 121 is integrated in the precipitator 112, takes the form of a brush and is situated at the centre of the precipitator 112. The corona electrode 121 has an extent in a direction opposite to the air flow direction through the air cleaning apparatus, which air flow direction is designated P in FIG. 2.

The casing 111 also accommodates a target electrode 122 in the form of a ring fitted in an air intake aperture of the casing 111.

An inlet grille/coarse mechanical filter 115 made of electrically insulating material is disposed between the target electrode 122 and the precipitator 112 as viewed in the axial direction C-C of the casing 111. The inlet grille/coarse filter 115 has a cylindrical circumference for adaptation to the precipitator 112 and the target electrode 122.

The diameters of the precipitator 112, the coarse filter 115 and the target electrode 122 are of the same order of magnitude. In the region of the end of the casing 111 which faces away from the target electrode 122, the casing 111 is provided with apertures 130 whose function is explained below.

The casing 111 and its components 112, 115, 121, 122 are intended for once-only use, i.e. the unit constituted by the casing 111 and its components 112, 115, 121, 122 is replaced when the user finds cause for doing so, e.g. when any of the components is so contaminated that cleaning is no longer considered sensible.

The air cleaning apparatus according to the alternative embodiment also comprises a permanent portion comprising a base element 131 with hooklike engaging means 132 which are adapted to cooperating with the apertures 130, i.e. the hooklike engaging means 132 and the apertures 130 constitute a releasable connection between the casing 111 and the base element 131. The centreline C-C constitutes also a centreline for the permanent portion and defines also the permanent portion's axial direction.

The permanent portion comprises a fan unit 113 recessed in the base element 131, i.e. the fan unit 113 is countersunk to a certain extent in the base element 131, in its axial direction C-C. The fan unit 113 comprises a fan blade 133 surrounded by a protective cage 134 which forms part of the fan unit 113. The fan unit 113 comprises also an electrical component 135 comprising a power source for the fan, and a high-voltage unit which generates the corona current between the corona electrode 121 and the target electrode. The high-voltage unit is connected to the corona electrode 121 and the target electrode 122 when the base element 131 of the permanent portion is assembled with the casing 111.

With regard to the materials of the various parts, we refer to what was stated above with regard to each of those parts. Also with regard to the ionisation of the incoming air, symbolised by the arrow P in FIG. 2, we refer to what was stated above with regard to corona current and to expansion of the ion clouds formed during the ionisation.

The invention claimed is:

1. An air cleaning apparatus for cleaning of indoor air/outdoor air, which apparatus comprises:
   an air flow duct, with an extent defining an axial direction, to accommodate air flow entering the apparatus in an air flow direction;
   an air-conveying fan unit disposed in the air flow duct;
   a high-voltage source (23);
   a precipitator (12; 112) with an air throughflow passage for air which is to be cleaned and located in the air flow duct;
   a unipolar corona electrode (21; 121) disposed adjacent one end of the air flow duct and connected to a first pole of the high-voltage source;
   a target electrode (22, 122) disposed in a spaced radial direction from the corona electrode (21; 121) such that the target electrode surrounds the air throughflow passage for the air passing between a periphery of the target electrode (22; 122) and the corona electrode (21; 121) which is to be cleaned and surrounds the air flow entering the apparatus,
   wherein the corona electrode (21; 121) is so disposed that ions generated at the corona electrode freely spread away from the corona electrode towards the target electrode; and
   an inlet grille/coarse filter disposed between the precipitator and the target electrode in the axial direction of the air flow duct, the inlet grille/coarse filter being made of an electrically insulating material.

2. An air cleaning apparatus according to claim 1, wherein, the corona electrode is disposed centrally in the air flow duct in a region of one end of the air flow duct,
   the target electrode is disposed close to the same end of the air flow duct.

3. An air cleaning apparatus according to claim 1, wherein the target electrode is disposed at constant distance from the corona electrode.

4. An air cleaning apparatus according to claim 1, wherein, the corona electrode is electrically connected to a negative pole of the high-voltage source, that the target electrode is connected to an opposite pole of the high-voltage source, and the polarity of the corona electrode in relation to earth potential is opposite to the polarity of the target electrode in relation to earth potential.

5. An air cleaning apparatus according to claim 1, wherein either the corona electrode or the target electrode or both of the corona and the target electrodes are connected to the high-voltage source via high-resistance resistors with a resistance greater than 1 Gohm.

6. An air cleaning apparatus according to claim 1, further comprising a permanent portion and an interchangeable portion, that the permanent portion comprises a fan unit and the high-voltage unit, wherein the interchangeable portion comprises the precipitator, the corona electrode and the target electrode.

7. An air cleaning apparatus according to claim 6, wherein the permanent portion comprises a base element, and the base element and the interchangeable portion comprise cooperating engaging means.

8. An air cleaning apparatus according to claim 2, wherein the target electrode is disposed at constant radial distance from the corona electrode.

9. An air cleaning apparatus according to claim 1, wherein either the corona electrode or the target electrode or both of the corona and the target electrodes are connected to the high-voltage source via high-resistance resistors with a resistance greater than 2 Gohm.

10. An air cleaning apparatus according to claim 1, wherein, the target electrode is, in terms of electrostatic field, substantially circular and symmetrical relative to the corona electrode.

11. An air cleaning apparatus according to claim 1, wherein, the target electrode has a ring shape.

12. An air cleaning apparatus according to claim 1, wherein,
    the target electrode is a circular ring and is symmetrical with respect to the corona electrode, and
    the target electrode is disposed in a region of a periphery of an inlet of the air flow duct.

13. An air cleaning apparatus according to claim 1, wherein,
    the corona electrode is connected to a first pole of the high-voltage source, and
    the target electrode is connected to a second pole of the high-voltage source.

14. An air cleaning apparatus according to claim 1, wherein,
    the air flow duct is a circular cylindrical casing,
    the precipitator is a circular cylindrical electrostatic precipitator disposed in the casing, and
    the corona electrode includes an axial extent disposed a center of a portion of the inlet grille/coarse filter which is pervious to air flow.

15. An air cleaning apparatus according to claim 14, wherein the air-conveying fan unit is disposed in the casing downstream of the precipitator, and the inlet grill is located adjacently between the target electrode and the precipitator.

16. An air cleaning apparatus according to claim 1, wherein the air-conveying fan unit is disposed in the casing upstream of the precipitator, and the inlet grill is located adjacently between the target electrode and the fan unit.

17. An air cleaning apparatus according to claim 1, wherein a majority of expansion of the ion cloud between the corona electrode (21) and the target electrode (22) takes place perpendicularly out from a plane which the target electrode (22) defines and in an opposite direction to the air flow direction, with a majority of the ion cloud generated at the corona electrode (21) reaching the target electrode (22) instead of migrating into a surrounding space in which the apparatus is situated.

18. An air cleaning apparatus according to claim 17, wherein the expansion of the ion cloud in the opposite direction to the air flow direction reaches at most a distance corresponding to a radial spacing between the corona electrode (21) and the target electrode (22).

19. An air cleaning apparatus for cleaning of indoor and outdoor air, which apparatus comprises:
- a circular cylindrical casing (11) which serves as an air flow duct defining an axial direction, an air flow direction, and an air throughflow passage;
- a circular cylindrical electrostatic precipitator (12) disposed in the casing, the precipitator being interchangeable;
- an air-conveying fan unit (13) disposed in the casing upstream of the precipitator;
- a high-voltage source (23);
- a unipolar corona electrode (21) with an axial extent disposed at an air inlet side of the casing and connected to a first pole of the high-voltage source;
- a target electrode (22) disposed in a spaced radial direction from the corona electrode (21; 121) such that the target electrode surrounds the air throughflow passage and surrounds the air flowing between a periphery of the target electrode and the corona electrode such that ions generated at the corona electrode freely spread away from the corona electrode towards the target electrode, wherein a majority of expansion of the ion cloud between the corona electrode (21) and the target electrode (22) takes place perpendicularly out from a plane which the target electrode (22) defines and in an opposite direction to the air flow direction, with a majority of the ion cloud generated at the corona electrode (21) reaching the target electrode (22) instead of migrating into a surrounding space in which the apparatus is situated; and
- an inlet grille/coarse filter disposed downstream of and adjacent the target electrode in the axial direction of the casing, the axial extent of the the corona electrode being disposed a center of a portion of the inlet grille/coarse filter which is pervious to air flow, and the inlet grille/coarse filter being made of an electrically insulating material.

20. An air cleaning apparatus according to claim 17, wherein an air-conveying fan unit is disposed in the casing downstream of the precipitator, and the inlet grille/coarse filter is located adjacently between the target electrode and the precipitator.

* * * * *